US012721646B2

(12) United States Patent
Vogele

(10) Patent No.: US 12,721,646 B2
(45) Date of Patent: Sep. 1, 2026

(54) INSTRUMENT FEEDING DEVICE AND USE OF A SPINDLE DEVICE IN AN INSTRUMENT FEEDING DEVICE

(71) Applicant: iSYS Medizintechnik GmbH, Kitzbühel (AT)

(72) Inventor: Michael Vogele, Schwabmünchen (DE)

(73) Assignee: Isys Medizintechnik GmbH, Kitzbühel (AT)

( * ) Notice: Subject to any disclaimer, the term of this patent is extended or adjusted under 35 U.S.C. 154(b) by 296 days.

(21) Appl. No.: 18/290,023

(22) PCT Filed: May 3, 2022

(86) PCT No.: PCT/EP2022/061826

§ 371 (c)(1),
(2) Date: Nov. 9, 2023

(87) PCT Pub. No.: WO2022/253505

PCT Pub. Date: Dec. 8, 2022

(65) Prior Publication Data

US 2024/0268861 A1 Aug. 15, 2024

(30) Foreign Application Priority Data

Jun. 1, 2021 (DE) ........................ 102021114151.6

(51) Int. Cl.
*A61B 17/34* (2006.01)
*A61B 17/00* (2006.01)

(52) U.S. Cl.
CPC .................... *A61B 17/3403* (2013.01); *A61B 2017/00402* (2013.01); *A61B 2017/3409* (2013.01)

(58) Field of Classification Search
CPC ...... A61B 17/3403; A61B 2017/00402; A61B 2017/3409; A61B 90/11; A61B 90/18;
(Continued)

(56) References Cited

U.S. PATENT DOCUMENTS 6,109,270 A * 8/2000 Mah ........................ A61B 90/11
128/924
2008/0177285 A1 7/2008 Brock et al.
(Continued)

FOREIGN PATENT DOCUMENTS

EP 230 309 8 B1 7/2016
JP 2016073882 A 5/2016
(Continued)

OTHER PUBLICATIONS

English Language Machine Translation of WO2020135748A1.
(Continued)

*Primary Examiner* — Shaun L David
*Assistant Examiner* — Cherie M Poland
(74) *Attorney, Agent, or Firm* — Lerner David LLP

(57) ABSTRACT

An instrument advancing apparatus for translationally and/or rotationally driving at least one first instrument is disclosed. The instrument advancing apparatus includes a guide device having at least one first axis body extending in a translational driving direction of the at least one first instrument. The apparatus further includes at least one first motor configured to be motor-driven along the first axis body and at least one second motor being motor-driven along the first axis body or along a second axis body which is aligned parallel to the first axis body. The first motor is connected or connectable to a first holding means for holding and/or moving the at least one first instrument. The second motor is connected or connectable to a second holding means for holding and/or moving the at least one first instrument or a second instrument. A use of a spindle device with double threads is also disclosed.

12 Claims, 14 Drawing Sheets

(58) Field of Classification Search
CPC .......... A61B 90/50; A61B 2017/00477; A61B 34/30; A61B 2090/508; A61B 2090/571
See application file for complete search history.

(56) References Cited

U.S. PATENT DOCUMENTS

| | | | | |
|---|---|---|---|---|
| 2013/0123759 | A1 | 5/2013 | Kang et al. | |
| 2015/0008815 | A1 | 1/2015 | Kuehl et al. | |
| 2015/0073339 | A1 | 3/2015 | Pacheco | |
| 2016/0278806 | A1* | 9/2016 | Vogele | A61B 90/11 |
| 2016/0331375 | A1 | 11/2016 | Shelton, IV et al. | |
| 2020/0093491 | A1 | 3/2020 | Kitamura | |
| 2020/0353596 | A1 | 11/2020 | Tseng et al. | |

FOREIGN PATENT DOCUMENTS

| | | | | |
|---|---|---|---|---|
| JP | 2020185662 | A | 11/2020 | |
| WO | WO 98/33451 | A1 | 8/1998 | |
| WO | WO 2009/000527 | A1 | 12/2008 | |
| WO | WO 2009/100527 | A1 | 8/2009 | |
| WO | WO-2015175200 | A1 * | 11/2015 | A61B 46/10 |
| WO | WO 2017/144172 | A1 | 8/2017 | |
| WO | WO-2019197056 | A1 * | 10/2019 | A61B 34/30 |
| WO | WO 2020/135748 | A1 | 7/2020 | |

OTHER PUBLICATIONS

English Language Machine Translation of WO2009000527A1.
English Language Machine Translation of EP2303098B1.
English Language Machine Translation of WO2017144172A.

* cited by examiner

INSTRUMENT FEEDING DEVICE AND USE OF A SPINDLE DEVICE IN AN INSTRUMENT FEEDING DEVICE

CROSS REFERENCE TO RELATED APPLICATIONS

This application is a national phase of International Application PCT/EP2022/061826, filed May 3, 2022, which claims priority to German patent application 102021114151.6, filed Jun. 1, 2021, the content of both of which is hereby incorporated by reference.

BACKGROUND OF THE INVENTION

Field of the Invention

The present invention relates to an instrument advancing apparatus for translationally and/or rotationally driving at least one first instrument. Furthermore, the invention relates to a use of a spindle device in an instrument advancing apparatus.

The present invention will be described hereinafter mainly in connection with medical instruments, in particular with a needle and a trocar. However, the invention can also be used in connection with non-medical instruments, for example laboratory instruments or measuring instruments.

Description of Related Art

Instrument advancing apparatuses are generally used to move instruments translationally and/or rotationally.

A wide variety of possibilities are known from the state of the art for implementing an instrument advancement or feed. Particularly when advancing medical instruments, very high demands are placed on the accuracy, reliability and sterilizability of the instrument advancing apparatus. Thus, numerous attempts have been made in the prior art to further develop and improve instrument advancing apparatuses taking these requirements into account.

For example, a device for controlled displacement movement and optional rotary movement of an instrument is known from EP 230 309 8 B1. In this case, the device has a linear actuating element which engages at a rear end of the instrument, the actuating element having a linear motor with an electromagnetic direct drive and a spindle which can be displaced relative to a stator and in which the instrument is configured to be guided.

However, the systems known from the prior art are all relatively complex and not sufficiently compact, in particular flat. The design implementation of the high requirements is reflected in a complex structure. Typically, the structure is then also no longer flat enough to be used in an imaging tube. In addition, the known systems can still be further improved, especially with regard to their accuracy and sterilizability.

BRIEF SUMMARY OF THE INVENTION

Based on the above prior art, it is the object of the present invention to provide an improved device which eliminates the above problems and disadvantages of the prior art. In particular, it is the object of the present invention to provide an instrument advancing apparatus which is characterized by a simple and functional structure.

In particular, the solution according to the invention is to provide an instrument advancing apparatus for translationally and/or rotationally driving at least a first instrument, wherein the instrument advancing apparatus comprises: a guide device having at least one first axis body extending in particular in a translational driving direction of the at least one first instrument; at least one first motor configured motor-driven along the first axis body; and at least one second motor configured motor-driven along said first axis body or along a second axis body aligned parallel to said first axis body, wherein said first motor is connected or connectable to a first holding means for holding and/or moving said first instrument, and wherein said second motor is connected or connectable to a second holding means for holding and/or moving said first instrument or a second instrument.

Thus, in a first alternative, the guide device comprises one axis body, wherein the first motor and the second motor are motor-driven along the one axis body. In a second alternative, the guide device has two parallel axis bodies, wherein the first motor is motor-driven along the first axis body and the second motor is motor-driven along the second axis body.

When the guide device has two axis bodies, the two axis bodies are fixed parallel to each other, i.e., fastened. This means that the two axis bodies are permanently arranged parallel to each other, i.e. they cannot be moved relative to each other. In this case, the guide device is configured in such a way that the guide device fixes the two axis bodies rigidly, i.e. not movable relative to each other. The guide device is a component that physically forms a unit and, in particular, is not formed by a plurality of components, for example arms, that are movable relative to one another. For example, in one configuration, the guide device comprises the two axis bodies and at least one, preferably two, connecting region(s) connecting the two axis bodies to each other. Particularly preferably, in this case, a connecting region is formed at an upper end and a connecting region is formed at a lower end of the two axis bodies.

The instrument advancing apparatus is generally attachable to a positioning arm.

Instrument advancement is understood as the motorized movement of an instrument, regardless of whether the instrument is moved translationally or rotationally. The moved instrument is preferably a medical or medical-technical instrument or a metrological or laboratory instrument. The instrument has a leading end, in the case of a medical instrument an end directed towards the patient. Typically, the instrument has a functional element at this leading end. This may be, for example, an opening in the case of a trocar, a needle tip in the case of a needle, a gripping jaw in the case of forceps, a probe head in the case of a probe, or a cutting edge in the case of scissors or a knife.

The functional element may be placed outside the body, on the surface of the body, or inside the body. The functional element can generally be diagnostic and therapeutic instruments of all types, which can be positioned during interventions and surgical procedures with a manual input device or automatically.

Depending on the applications, different designs are possible in terms of degree of freedom, stability, precision, material compatibility for imaging procedures, etc.

Examples for applications outside the body: guiding and positioning of an optical sensor, e.g. a microscope or exoscope: guiding and positioning of a radiation source or a laser or therapy beam; guiding of a gamma detector.

Examples of applications on the body surface: guiding and positioning of an ultrasound transducer on the skin surface; guiding and positioning of implants and injection needles and probes.

Examples of applications on the inside of the body: Guiding and positioning of an endoscope; guiding and positioning of (trocar) needles and needle-like instruments and probes for diagnosis and therapy (e.g., soft tissue and bone biopsy needles; e.g., ablation needles for radiofrequency ablation/microwave ablation/laser ablation probes/cryotherapy probes/irreversible electroporation/"seeds" for radiation therapy, etc.; e.g., drills, grasping forceps, scissors, scalpels, and other surgical instruments; e.g., hypodermic needles for local application of a drug); guiding and positioning catheters and catheter-like instruments in vessels and cavities; guiding and positioning implants, electrodes, etc.

The above list are only examples of diagnostic and therapeutic applications. Essentially, all diagnostic and therapeutic procedures in which diagnostic and therapeutic instruments/devices have to be guided and positioned can be supported. In this context, the device according to the invention is, due to various unique features—in particular the compactness and the precise instrument guidance close to the patient—naturally mainly aimed at minimally and microinvasive, image-guided diagnostic and therapeutic procedures, i.e. diagnostic and therapeutic procedures in which operations are primarily performed percutaneously, intravascularly or through already existing body orifices and in which (novel) miniaturized instruments and devices (so-called "smart instruments") are used. All medical imaging and medical navigation systems can be used to localize the instrument or robot on or in the patient. When using live or real-time imaging, compactness and the selection of appropriate materials are of crucial importance in order to avoid space problems and image artifacts. In addition to the known advantages of using robotic technology, the use of the device according to the invention allows much more precise and efficient work, especially in difficult, anatomical conditions, thanks to the possibility of (live) imaging for position control at any time. In addition, ergonomics and patient accessibility also play a major role, since the space inside the "tube" (or gantry) or at the operating table is often very limited. By "teleworking" at a distance and reducing diagnostic/therapeutic time, both the patient and the operator can be protected from radiation damage and other negative influences when using equipment with ionizing radiation, hazardous substances, etc.

Driving is understood to be an initiation of movement of the instrument. For this purpose, the translatory or rotating movement is transferred to the instrument. Translational driving does not necessarily mean that the instrument or, more precisely, the leading end of the instrument performs a purely translational movement. Rather, it is also conceivable and, depending on the application, desirable that the leading end executes an arcuate movement path when driven translationally. This is possible, for example, when using a trocar and by inserting a needle or probe with a curved or angulable leading end. Alternatively, a flexible needle with a specific cut, a so-called steerable needle, could also be used. Due to the shape of the leading end, a radial force acts on the leading end when the instrument is moved through a body, so that the leading end moves along an arcuate path of motion.

The guide device is configured to guide the movements of the motors. For this purpose, the guide device has the at least one axis body that specifies the direction of movement of the motor. The translational driving direction of the instrument is the direction in which the translational motion for driving the instrument is effected. Since the motors move along the at least one axis body, the translational driving direction corresponds to the main extension direction, i.e., the axial direction, of the at least one axis body.

The axis body is preferably a polygonal axis, in particular a square axis. Particularly preferably, the axis body is made of ceramic. The advantage with a ceramic axis body is that it is compatible for magnetic resonance imaging (MRI) or X-ray, as well as being low-wear.

Since the motors are connected or connectable to corresponding holding means, the holding means move together with the motors. For example, the motors each have a housing on which the holding means are directly or indirectly arranged.

The holding means are configured to hold the instruments and to transmit rotational or translational movements to the instruments. Preferably, the holding means are not assigned to a fixed point or area of the instruments, but are configured to hold the instruments at any point or area and to transmit rotating or translatory movements. This is of course dependent on the instrument used. In particular, however, it is possible to hold a trocar and a needle at any point.

Particularly preferably, the holding means here is configured to hold the instrument as close as possible to the leading end of the instrument. This makes it possible to achieve a particularly high degree of precision for guiding the instrument. Transferred to a medical instrument, the instrument can then be gripped by the holding device in the vicinity of a skin entry point on the patient. This provides a significant advantage over the known robotic systems. The known robotic systems basically hold and move the instruments at a distal end, relative to the entry point on the patient. Thus, the distance between the parts holding and moving the instrument and the entry point is large. This in turn leads to inaccuracy in the known systems.

In contrast, the present instrument stabilizing device is configured in such a way that the instruments can be held and moved at a proximal region, in particular a leading end. This results in a particularly high precision.

In the simplest embodiment, the holding means fix the instrument to be held, for example by means of clamping. The fixed area of the instrument then moves together with the holding means. In more complex designs, the holding means can be used to convert the translatory movements of the motors into a rotating movement.

The advantage of the instrument advancing apparatus is, in particular, that it is extremely simple and compact in design due to the motors moving along axis bodies. At the same time, the movements of such motors can be precisely controlled. Overall, this makes it possible to achieve an instrument advancing apparatus with a low weight and a very compact design, which also makes it possible to use it remotely in the narrow tube of an MR device.

A simplified variant of the instrument advancing apparatus for translationally and/or rotationally driving at least one first instrument comprises: a guide device having at least one first axis body extending in a translational driving direction of the at least one first instrument; and at least one first motor configured to be motor-driven along the first axis body, the first motor being connected or connectable to a first holding means for holding and/or moving the first instrument.

In this embodiment, the instrument advancing apparatus does not necessarily have two motors. Even with only one motor, a simple, compact and functional structure is obtained. In this regard, the instrument advancing apparatus with one motor is a separate inventive subject matter. All of the following aspects, in particular the embodiments or further embodiments according to the invention, can also be applied to the single-motor variant, provided that they do not necessarily require at least two motors.

In a preferred embodiment of the present invention, the instrument advancing apparatus comprises at least a third motor configured to be motor-driven along the first axis body, along the second axis body, or along a third axis body aligned parallel to the first axis body and the second axis body.

Thus, an alternative is described herein in which the guide device may correspondingly have three parallel axis bodies. The instrument advancing apparatus may comprise further axis bodies and/or motors.

According to an advantageous further development of the invention, the third motor is configured with a third holding means for holding and/or moving the first instrument or the second instrument.

By means of the third motor, in particular with its third holding means, on the one hand the range of movement of the already existing instruments, i.e. the first instrument and optionally the second instrument, can be increased. On the other hand, the third holding means can also be used to hold and move another instrument.

Exemplarily, the first and the second motor can be assigned to the first instrument, for example a needle, and the third motor can be assigned to a second instrument, for example a trocar, so that needle and trocar can be moved independently of each other.

The instrument advancing apparatus may have further motors that are either stacked on the already formed axis bodies or are configured on further axis bodies that are configured parallel to the already formed axis bodies. In this way, the range of motion of the already existing instruments can be extended even more or further instruments can be arranged.

Overall, parallel or time-shifted movements of the motors allow paths to be traversed precisely and single-axis and multi-axis movements to be achieved in a very confined space.

A particularly advantageous embodiment of the present invention provides that the motors are configured as piezo-motors.

In other words, the first motor and the second motor and optionally the third motor and any further motor are configured as piezo motors. A piezomotor uses the piezoelectric effect to generate motion. The motors used are piezomotors with direct linear drive, in which no conversion of rotational motion to linear motion is necessary.

In simplified terms, the piezomotor has at least one electromechanical material in the form of feet that changes under the influence of an electric field. The axis body is held by means of the feet, wherein preferably at least two pairs of feet, each having two opposing feet, are arranged on opposite sides of the axis body. In this case, the axis body is held by a contact pressure of the feet. The two pairs of feet move out of phase so that the axis body is passed from the rear pair of feet to the front pair of feet. This also allows the motor to move along the axis body.

The electromechanical material is preferably a piezoceramic. This makes it possible to achieve a good tribological pairing for long operation without significant wear, particularly in combination with an axis body made of ceramic.

The piezomotor has a low weight and is compact, so that the entire instrument advancing apparatus can have a simple and lightweight structure. In addition, by means of the piezomotor, extremely precise and backlash-free movement of the instruments is possible. For example, such fine microsteps can be performed by means of the piezomotor that it is possible to accurately position the instrument at the cellular scale, for example such microsteps are smaller than 1/10000 mm. Furthermore, the piezomotor can be manufactured without metal, so that it is configured to be MRI compatible and X-ray compatible.

Another advantage of the piezo motor is that the feed force is easily limited by the contact pressure of the feet on the axis body. If the counter pressure acting on the instrument is too high, the axis body is not held sufficiently by the feet and slips. This force limitation makes it possible to always operate an instrument with the same force. For example, it is thus possible by means of the instrument advancing apparatus to always operate an ultrasound probe with a specific, in particular optimal, contact pressure. The slippage when the counter pressure is too high is also suitable, for example, for determining the counter pressure acting on an instrument. For this purpose, the target travel distance of the piezo motor is compared with the actual travel distance reduced by slipping.

In general, a piezo motor can be installed with a contact pressure suitable for the area of application. Alternatively, it would be conceivable for the contact pressure of the feet to be adjustable. In this way, the maximum feed force can be adjusted.

Another advantageous effect of the piezo motor is that the piezo motor performs slight vibrations when moving. These fine vibrations ensure particularly high precision on the tool. In addition, the vibrations can have other positive effects in certain applications. An example of this is biopsy removal during a bone or soft tissue biopsy. A vibrating needle can facilitate the penetration of the needle into the tissue or bone. The vibrating motion of the needle tip can further ensure that blood-bearing tissues can evade the needle as it penetrates. In the case of a biopsy, the vibration also makes it easier to detach and remove the sample.

Furthermore, the vibrations have a synergistic effect, particularly in conjunction with a spindle device, since the fine vibrations of the piezo motor ensure outstanding smoothness and precision in the spindle device.

According to an advantageous further development of the invention, the motors are configured to be wirelessly drivable and/or operable.

A wireless drive preferably comprises the use of an accumulator. Preferably, the accumulator is configured with a charging coil for wireless charging of the accumulator. It is thus sufficient to provide cables from the accumulator to the motors, the cables being housed together with the accumulator and the motors, for example, under a sterile film. This makes it easier to implement a hygienic sterile concept, since the cables do not have to be routed to the outside. In addition, for example, a risk in the operating room emanating from cables is reduced.

If the motors are configured for wireless operation, they are connected to corresponding receivers which receive control signals from transmitters arranged on an input unit. The controlling input unit can thus be arranged at a location remote from the motors to be controlled. This can enable simpler and better operability. In particular, in conjunction with monitoring by an imaging device, such as a camera or an MRI tube, remotely controllable movement of the instrument advancing apparatus or the instruments held by its holding means can be provided, for example, in an MRI or X-ray apparatus.

In another embodiment of the present invention, the instrument advancing apparatus includes a spindle device for rotationally moving the first instrument and operatively connected to at least one of the holding means.

A spindle device is generally understood to be a body formed with at least one thread for converting a translational motion into a rotational motion or vice versa. If required, the spindle or thread can also be configured asymmetrically, i.e. with at least one thread section with a flatter thread pitch and with at least one thread section with a steeper thread pitch.

By means of the spindle, a translational movement of the motors can be easily and precisely converted into a rotational movement of the instrument.

According to an advantageous further development of the invention, the spindle device is configured to interact with the first holding means and the second holding means.

When the spindle device is connected to two holding means, the range of motion of the first instrument connected to the spindle device can be increased.

In a further advantageous embodiment of the invention, the spindle device is configured as a hollow body and has at least one thread, wherein the first instrument can be arranged and fixed in a cavity of the hollow body.

The first instrument is preferably arranged passing through the cavity or the hollow body and is arranged on the spindle device in a rotationally fixed manner by means of a fixing device. Thus, a rotating movement of the spindle device is easily transferred to the first instrument. The fixing device may be, for example, a locking screw. For example, the spindle device is configured at least substantially as a hollow cylinder. The at least one thread is preferably arranged on an outer circumferential surface of the hollow body, in particular of the hollow cylinder.

In a preferred embodiment of the invention, the spindle device has two preferably counter-rotating threads.

In a particularly preferred further embodiment, the first holding means and/or the second holding means has a guide member which can be guided in the at least one thread.

The spindle and the guide member are preferably configured to be self-locking, so that movement does not occur without an external force influence.

The guide member can be, for example, a pin or a ball body. If ball bodies were used, a ball screw would be conceivable.

By means of two counter-rotating threads, it is possible simply and precisely to transmit both a rotary motion and a translatory motion via the spindle. For this purpose, the first holding means, for example by means of its guide member, is in operative connection with one thread and the second holding means, for example by means of its guide member, with the other thread. If the two holding means are moved in different directions, for example by moving only one of the holding means, this causes the spindle to rotate. If the two holding means are moved in parallel, i.e. at the same speed in the same direction, this causes translation of the spindle without rotation. Thus, the double-threaded spindle according to the invention serves to transmit both rotational and translational movements in an uncomplicated manner by means of fewer components. As an alternative to two counter-rotating threads, two co-rotating threads can also be used. In this case, the threads can have different pitches.

According to an advantageous further development of the invention, the spindle device and the holding means are configured as disposable articles. As disposable articles, sterile articles for medical applications can be easily provided with maximum freedom from contamination.

A particularly advantageous embodiment of the present invention provides that the motors each comprise fastening means for releasably fastening the respective holding means.

Thus, the first motor has a first fastening means for releasably fastening the first holding means, the second motor has a second fastening means for releasably fastening the second holding means, and optionally the third motor has a third fastening means for releasably fastening the third holding means. Of course, this also applies to any additional motor.

Due to the releasable fastening, the holding means can be easily separated from the motor at a later time and then disposed of, for example. For example, the releasable fastening means may be a latching means or a clipping means. Such fastening means can in particular also be released quickly and without the aid of a tool.

According to an advantageous further development of the invention, the fastening means each comprise a fastening unit for interacting with a complementarily shaped counter unit of the respective holding means.

The fastening unit is, for example, a receptacle for interacting with a complementarily shaped body of the holding means as a counter unit. In this way, a particularly simple and secure, in particular form-fitting fastening of the holding means to the fastening means is achieved.

A further embodiment of the present invention provides that the fastening unit and the counter unit have rounded corners and edges, so that they are suitable for non-destructive clamping of a sterile film surrounding at least the motors.

This allows a sterile film to be positioned between the holding means, the instruments, and optionally the spindle on one side and the remaining part of the instrument advancing apparatus on the other side. Thus, the remaining part of the instrument advancing apparatus can be easily separated in a sterile manner by means of the foil. The parts arranged outside the foil, i.e. the holding means, the instruments and optionally the spindle are either easy to sterilize or at least partially configured as disposable articles. In particular, the configuration as disposables, in combination with the film, results in a particularly safe and reliable sterile concept. All more expensive components, such as motors, axis bodies or, for example, the control system, are located behind the sterile film or cover. The few and simply designed disposable items can be manufactured inexpensively, exchanged and fastened to the fastening means with the sterile film in between.

According to an advantageous further development of the invention, the first instrument and/or the second instrument are medical instruments.

The advantages according to the invention can be used particularly well in connection with medical instruments. Such medical instruments may be diagnostic instruments as well as therapeutic instruments. For example, they may be an imaging instrument, a radiation therapy instrument, a drug delivery system, or a surgical instrument. If the medical instruments are used together with an X-ray apparatus, preferably all components located in the X-ray beam are made of plastic.

In another advantageous embodiment of the invention, the first instrument is a needle-shaped instrument and the second instrument is a tubular instrument, wherein the first instrument can be passed through the second instrument.

By means of the tubular instrument, the needle-shaped instrument can be safely guided into a body cavity of a patient. The needle-shaped instrument may be, for example, a puncture needle, injection needle, or probe. The tubular instrument may be, for example, a trocar. The tubular instrument and the needle-shaped instrument may be configured to be rigid or flexible. If both instruments or at least the needle-shaped instrument are configured to be flexible, arcuate movement of the two elements or at least the needle-shaped instrument is possible. For this purpose, the corresponding instrument has an obliquely shaped, curved or angulable leading end. Due to a radial force acting on the leading end during movement, the leading end deviates from a linear movement path to an arcuate movement path. In a preferred embodiment, the tubular instrument is flexible. This allows the tubular instrument to follow movements, such as respiratory movements, of a patient, and the needle-shaped instrument to be simultaneously deployed with positional accuracy at a predetermined point on the patient.

In a particularly preferred embodiment of the invention, the guide device comprises an instrument stabilizing device for stabilizing a leading end of the first instrument and or the second instrument.

In this case, the instrument stabilizing device is preferably located close to the patient's skin entry point, allowing the instruments to be guided close to the patient. This can further increase precision.

In another advantageous embodiment of the invention, the instrument advancing apparatus comprises at least one first position sensor arranged on the first motor and at least one second position sensor arranged on the second motor.

By means of the at least two position sensors, the relative movements of the motors with respect to each other and thus of the instruments can be measured. The sensors may, for example, be Hall sensors, magnets, optical markers or RFID chips. Furthermore, it is conceivable that further sensors are arranged on the instrument advancing apparatus which, for example, measure deformation of the instruments. In particular, strain gauges can be arranged on the instrument advancing apparatus for this purpose. Furthermore, gyro sensors may also be provided.

Furthermore, it is the object of the present invention to specify a use of a component, in particular a spindle device, in an instrument advancing apparatus, by means of which it is also possible to eliminate the disadvantages of the prior art.

The solution according to the invention consists in particular in providing the use of a spindle device, in particular with double thread, in an instrument advancing apparatus, namely for converting a translatory movement of a holding means of the instrument advancing apparatus into a rotary movement in such a way that by means of the spindle device an instrument, in particular a medical instrument, can be rotated.

The instrument advancing apparatus is preferably one of the instrument advancing apparatuses described above. Thus, the aspects and advantages already described in connection with the individual instrument advancing apparatuses are equally valid and transferable to the use and are not repeated individually here.

Preferably, the spindle device is configured to interact with the first holding means and the second holding means. In this way, the range of movement of the instrument connected to the spindle device can be increased.

Further preferably, the spindle device is configured as a hollow body having at least one thread, preferably two threads, wherein the first instrument can be arranged and fixed in a cavity of the hollow body. The at least one thread is preferably arranged on an outer circumferential surface of the hollow body, which is designed in particular as a hollow cylinder.

In a preferred embodiment of the invention, the hollow body has two counter-rotating threads, wherein the first holding means can be guided in one of the threads by means of a guide member and the second holding means can be guided in the other thread by means of a further guide member.

As already described, it can be easily implemented in such a way that the spindle transmits both a rotary motion and a translatory motion to the instrument.

In this regard, the spindle device constitutes an independent inventive subject matter.

The instrument advancing apparatus is suitable for a wide variety of applications. For example, the instrument advancing apparatus can be fastened directly to a positioning arm, in particular a positioning arm as described in DE 20 2020 107 591 U1. Alternatively, the positioning device can be fastened indirectly to the positioning arm. In this case, a fine positioning device, such as known from US 2021 001 556 4 A1, can be arranged between the positioning arm and the instrument advancing apparatus. Further alternatively, the instrument advancing apparatus may be used only with the fine positioning apparatus and without a positioning arm. In principle, the instrument advancing apparatus is not limited to any of the applications shown herein, but may be used in other environments and with connectors.

An independent inventive subject matter is provided by a force conversion device for an instrument advancing device. The force conversion device comprises: a spindle device having at least one thread; and at least one, preferably two, guide members guidable in the at least one thread and configured to be connectable or connected to a motor, in particular a linear motor.

Preferably, the spindle device is one of the spindle devices described above, so that all aspects are transferable here. In particular, the spindle device has two counter-rotating threads. Preferably, the guide member is one of the guide members described above, so that all aspects are transferable here as well. The linear motor may, for example, be a stepper motor or piezo motor.

Another independent inventive subject matter is provided by a sterile instrument holding device. The sterile instrument holding device has a plurality of disposable articles and a plurality of reusable articles configured to be separable from each other by means of a sterile film, wherein at least some of the reusable articles have fastening units having rounded corners and edges, and at least some of the disposable articles have counter units having rounded corners and edges that are releasably engageable with the fastening units.

This allows the sterile film to be disposed non-destructively for separation between the disposable articles and the reusable articles. The instrument holding device may be one of the aforementioned instrument advancing devices, so that all aspects are transferable here. The disposable articles and the reusable articles may be any of the aforementioned components. In particular, the disposable articles may be holding means, instruments or the spindle. The reusable items may be the remaining part of the instrument advancing apparatus, in particular the motors and axis bodies.

Thus, all of the more expensive components, such as motors, axis bodies or, for example, the control system, can be located behind the sterile film or cover. The few and simply designed disposable items can be manufactured inexpensively, replaced and fastened to the fastening means with the sterile film interposed.

A further independent inventive subject matter relates to a measuring system for monitoring an instrument advancing device. In this regard, the measuring system may comprise at least one first position sensor arranged on a first motor and at least one second position sensor arranged on a second motor, wherein the first motor is connected or connectable to a first holding means for holding and/or moving a first instrument, and wherein the second motor is connected or connectable to a second holding means for holding and/or moving the first instrument or a second instrument.

The instrument advancing device may be one of the aforementioned instrument advancing devices, so that all aspects are transferable here.

By means of the at least two position sensors, the relative movements of the motors with respect to each other and thus of the instruments can be measured. The sensors may be Hall sensors, magnets, optical markers or RFID chips, for example. Furthermore, it is conceivable that further sensors are arranged on the instrument advancing apparatus which, for example, measure deformation of the instruments. In particular, strain gauges can be arranged on the instrument advancing apparatus for this purpose. Furthermore, gyro sensors may also be provided.

The sensors may in particular be optical markers that can be detected by means of a camera. The camera can be configured as an inside-out system or as an outside-in system.

Further advantageous embodiments and combinations of features of the invention result from the following detailed description and the entirety of the patent claims.

BRIEF DESCRIPTION OF THE SEVERAL VIEWS OF THE DRAWINGS

Further advantages features and details of the various embodiments of this disclosure will become apparent from the ensuing description of a preferred exemplary embodiment or embodiments and further with the aid of the drawings. The features and combinations of features recited below in the description, as well as the features and feature combination shown after that in the drawing description or in the drawings alone, may be used not only in the particular combination recited but also in other combinations on their own without departing from the scope of the disclosure. The following is an advantageous embodiment of the invention with reference to the accompanying figures, wherein.

Generally, the same parts are provided with the same reference signs in the figures.

DETAILED DESCRIPTION OF THE INVENTION

Figure 1:
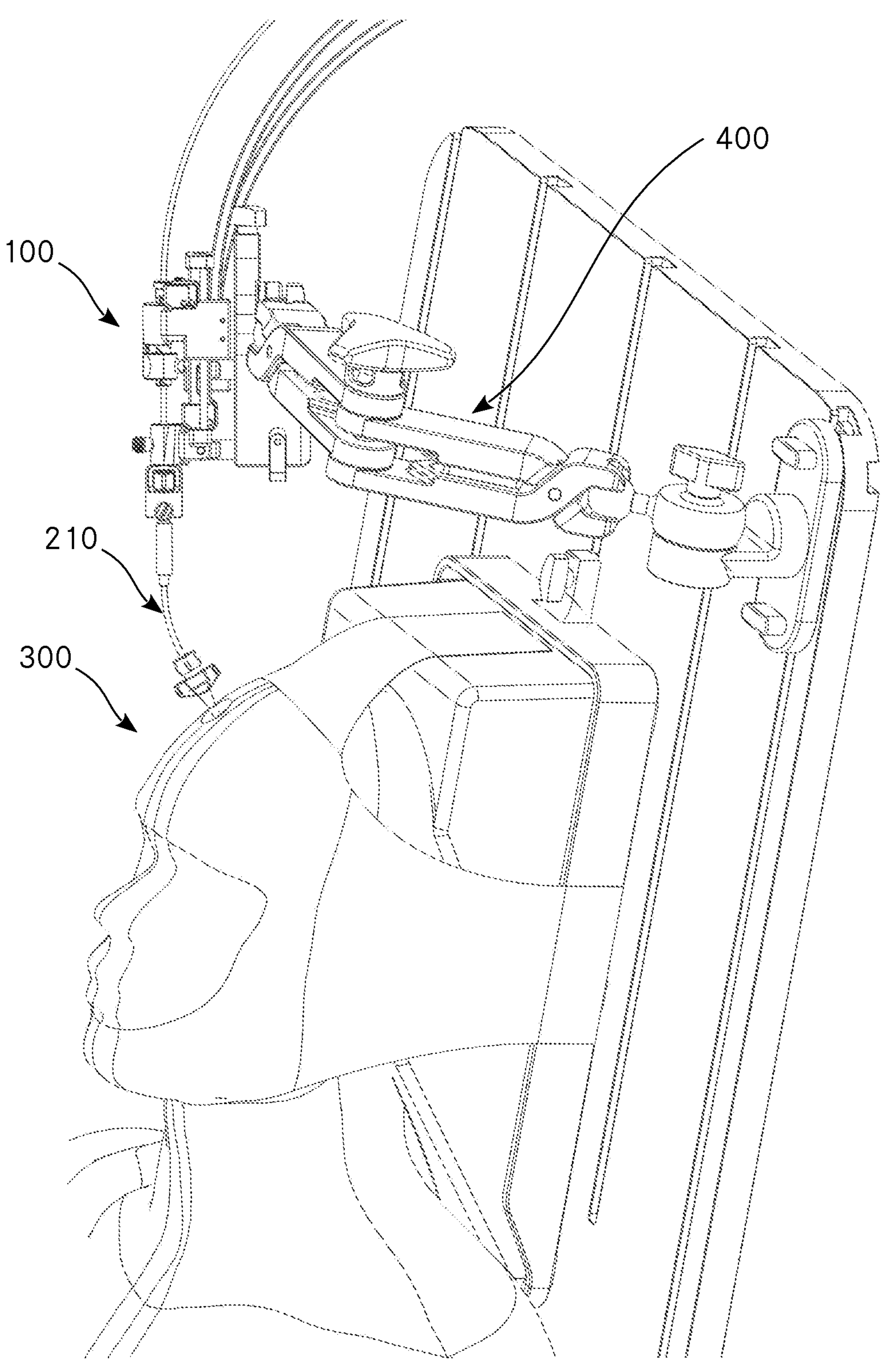
FIG. 1 depicts a perspective view of an instrument advancing apparatus according to the invention, which is attached to a positioning arm for treating a patient.

The subject-matter described in the following will be clarified by means of a description of those aspects which are depicted in the drawings. It is however to be understood that the scope of protection of the invention is not limited to those aspects described in the following and depicted in the drawings; to the contrary, the scope of protection of the invention is defined by the claims. Moreover, it is to be understood that the specific conditions or parameters described and/or shown in the following are not limiting of the scope of protection of the invention, and that the terminology used herein is for the purpose of describing particular aspects by way of example only and is not intended to be limiting.

Unless otherwise defined, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

Non-limiting aspects of the subject-matter of the present disclosure will be described by way of example with reference to the accompanying figures, which are schematic and are not intended to be drawn to scale. For purposes of clarity, not every component is labelled in every figure, nor is every component of each aspect of the invention shown where illustration is not necessary to allow those of ordinary skill in the art to understand the invention.

The following description will be better understood by means of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

FIG. 1 shows a perspective view of an instrument advancing apparatus 100 according to the invention for advancing a first instrument 210 when treating a patient 300. Exemplarily, the instrument advancing apparatus 100 is attached to a positioning arm 400, the arm elements of which—as described in detail in DE 20 2020 107 591 U1—are configured in a pincer-like manner and the three joints of which can be centrally locked or released by means of a rotary handle engaging the central joint.

Figure 2:
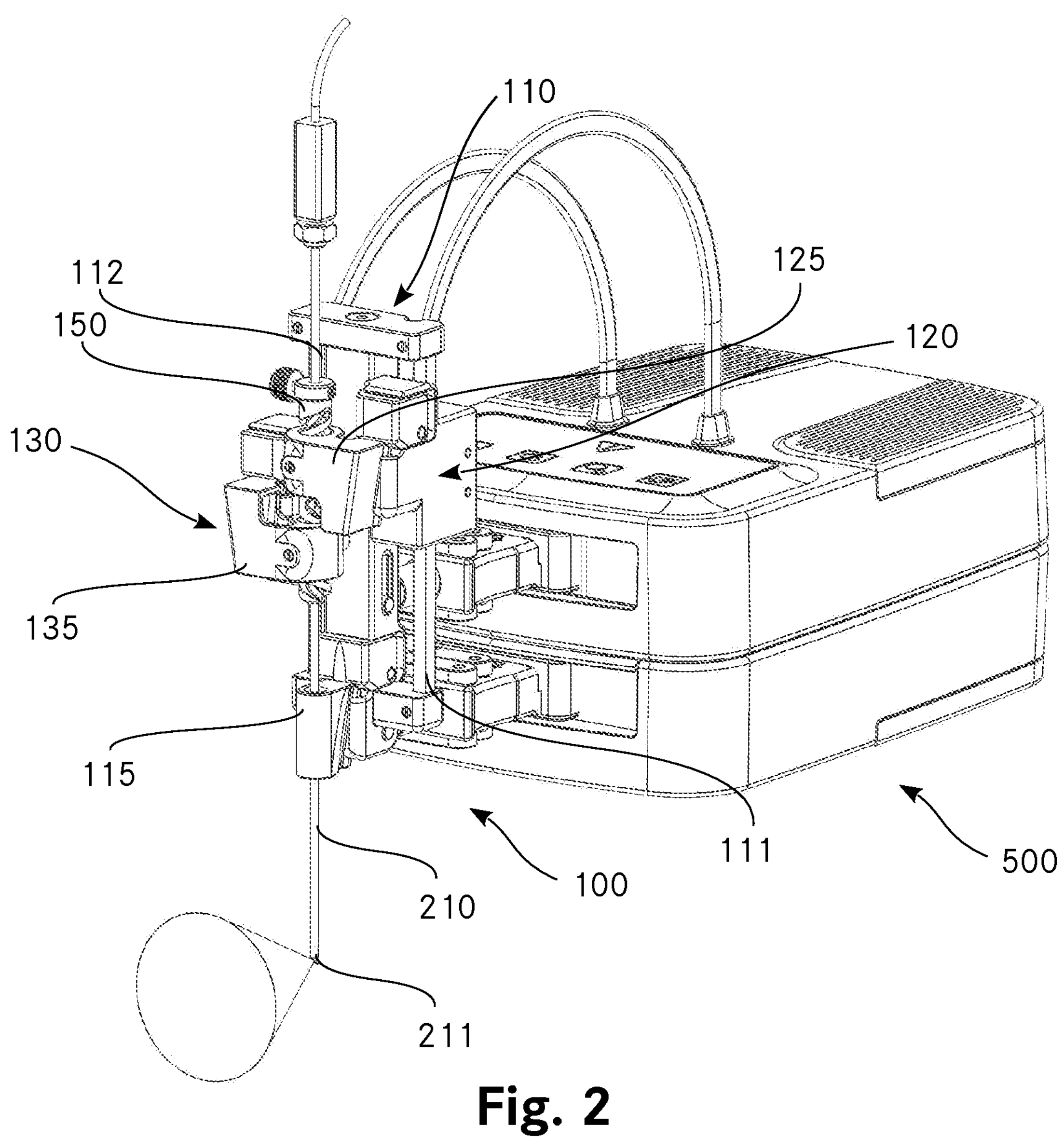
FIG. 2 depicts a perspective view of an instrument advancing apparatus according to the invention in a dual motor design.

FIG. 2 shows a perspective view of the instrument advancing apparatus 100 according to the invention in a dual-motor embodiment. In the embodiment shown, the instrument advancing apparatus 100 is attached to a fine positioning apparatus 500, as an example.

The instrument advancing apparatus 100 shown in FIG. 2 is configured to translationally and/or rotationally drive the first instrument 210. Here, the first instrument 210 is exemplarily a probe having a probe head at a leading end 211.

The instrument advancing apparatus 100 comprises a guide device 110 having a first axis body 111 and a second axis body 112. Both axis bodies 111 and 112 extend in a translational driving direction of the first instrument 210.

A motor 120, 130 is arranged on each of the two axis bodies 111 and 112. More specifically, a first motor 120 is arranged on the first axis body 111 to be movable relative to the first axis body 111, and a second motor 130 is arranged on the second axis body 112 to be movable relative to the second axis body 112.

The first motor 120 is connected to a first holding means 125 for holding and/or moving the first instrument 210. The second motor 130 is connected to a second holding means 135 for holding and/or moving the first instrument 210. As can be further seen in FIG. 2, both the first holding means 125 and the second holding means 135 are connected to a spindle device 150. Thus, by moving the motors 120 and 130, it is possible not only to move the first instrument 210 in a translational direction, but also to move it in a rotational direction. The movement sequence of each motor will be described in more detail later with reference to FIGS. 8-14.

An instrument stabilizing device 115 for stabilizing a leading end of the first instrument 210 is disposed at a leading end of the guide device 110. Thus, the first instrument 210 can be stabilized close to a skin entry point of the patient 300.

Figure 3:
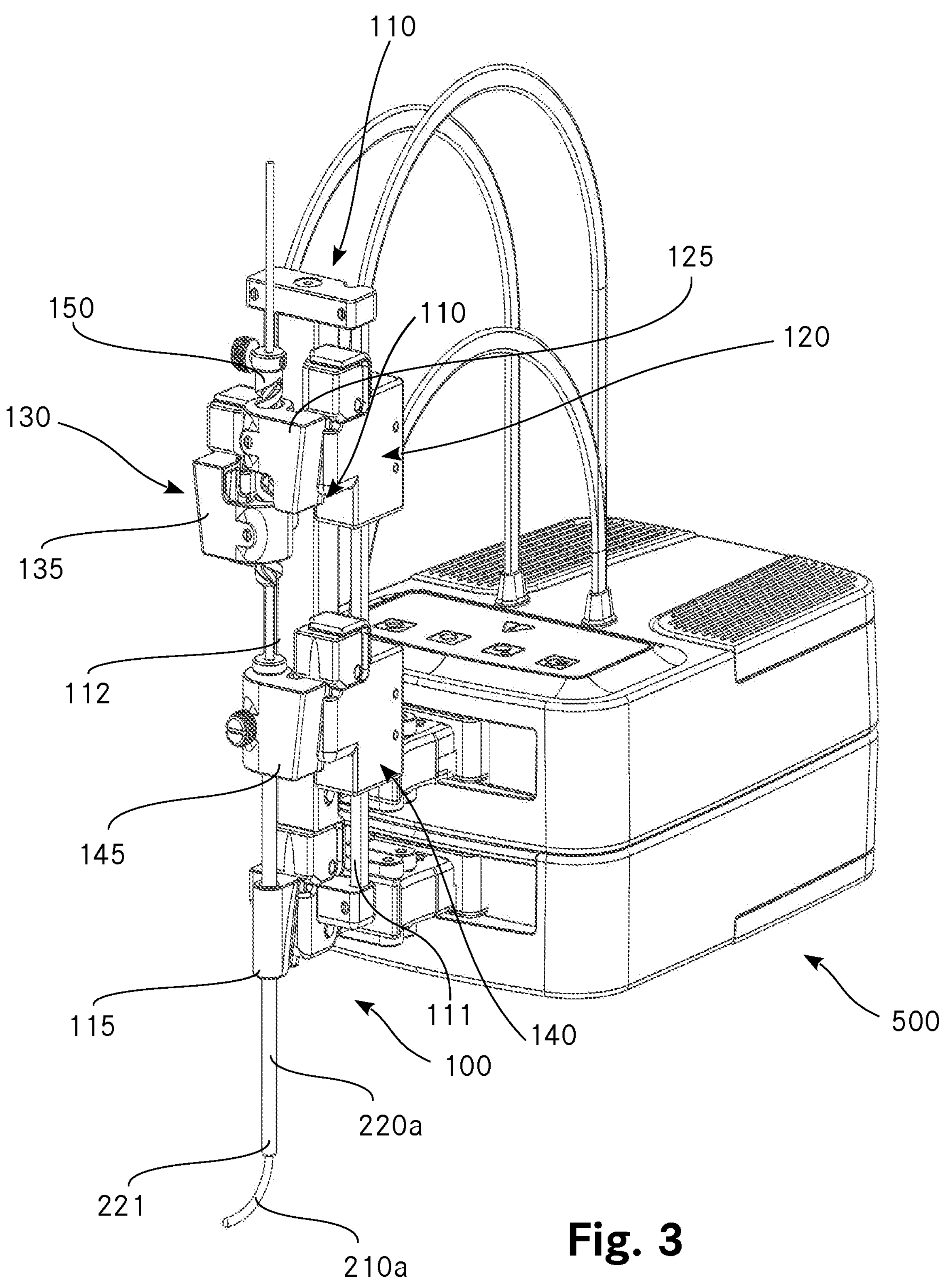
FIG. 3 depicts a perspective view of an instrument advancing apparatus according to the invention in a three-motor design.

FIG. 3 shows a perspective view of the instrument advancing apparatus 100 of the invention in a three-motor embodiment. In the embodiment shown, the instrument advancing apparatus 100 is again exemplarily attached to a fine positioning apparatus 500.

Unlike the instrument advancing apparatus 100 shown in FIG. 2, the instrument advancing apparatus 100 shown in FIG. 3 drives a first instrument 210 and a second instrument 220. The first instrument 210 is a needle-shaped instrument 210*a* and the second instrument 220 is a tube-shaped instrument 220*a*. The needle-shaped instrument 210*a* is guided within the tube-shaped instrument 220*a* to be securely insertable into a body cavity of a patient 300. The needle-shaped instrument 210*a* exits a leading end 221 of the tubular instrument 220*b*.

In turn, the guide device 110 includes two axis bodies 111 and 112 and the instrument stabilizing device 115. The two motors 120 and 130 are used to move the first, tubular, instrument 210*a*. In this regard, the two holding means 125 and 135 are again connected to the spindle device 150 so that the tubular instrument 210*a* can be driven translationally and rotationally.

In addition to the embodiment shown in FIG. 2, the guide device 110 shown in FIG. 3 has a third motor 140. The third motor 140 is configured to be movable on and relative to the first axis body 111. However, it would also be conceivable for this to be arranged on the second axis body 112 or another axis body not shown.

The third motor 140 is configured with a third holding means 145 for holding and moving the second, tubular, instrument 220*a*. Thus, the second instrument 220 can be moved independently of the first instrument 210.

Figures 4, 5:
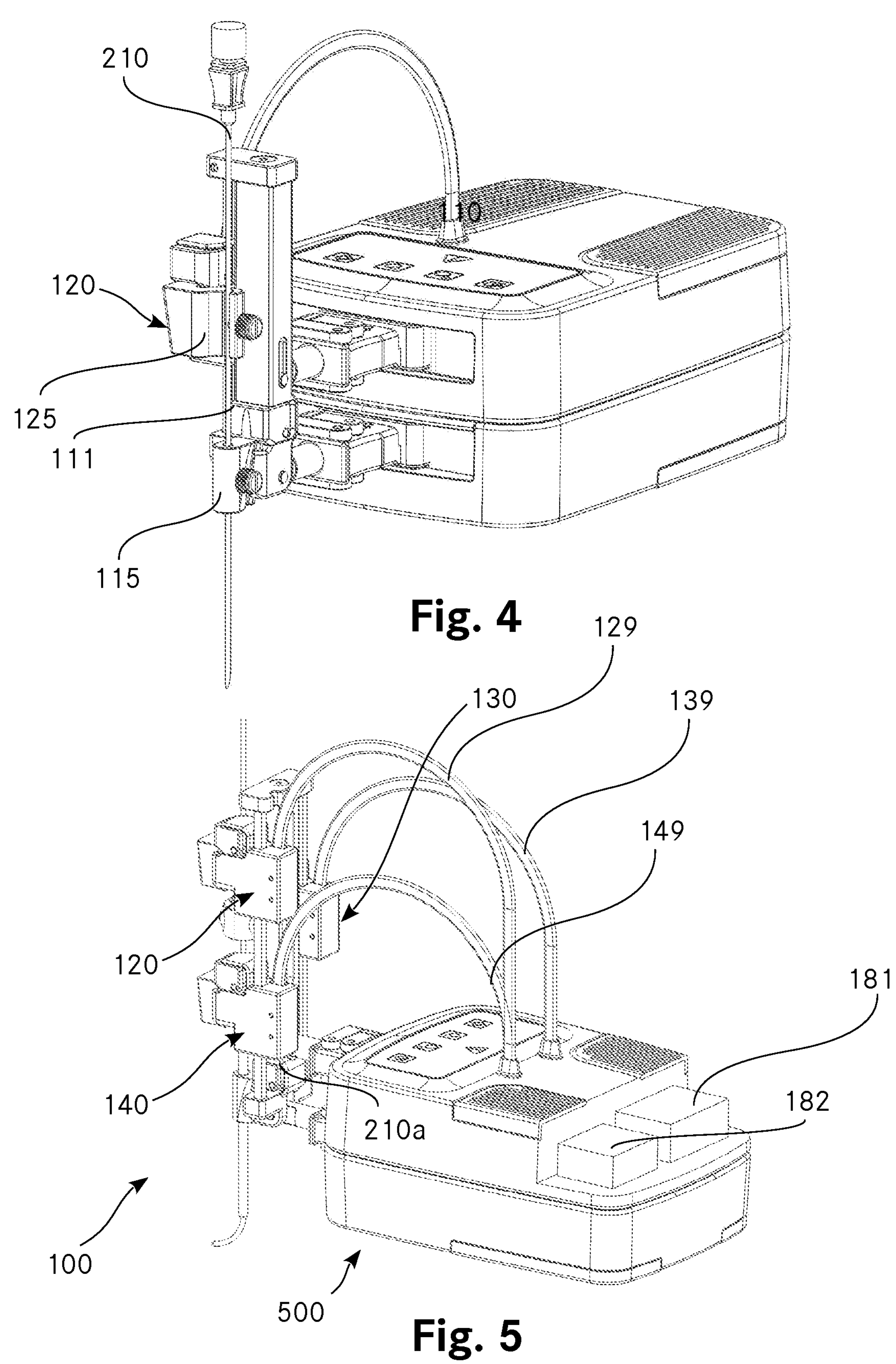
FIG. 4 depicts a perspective view of an instrument advancing apparatus in a single motor design.
FIG. 5 depicts a perspective view of an instrument advancing apparatus according to the invention from the rear.

FIG. 4 shows a perspective view of the instrument advancing apparatus 100 in a single motor version. Here, the guide device 110 comprises only the first axis body 111 and the first motor 120, which is movable along the first axis body 111. Accordingly, only a first instrument 210 is fastened to the first motor 110 by means of the first holding means 125. Again, the instrument stabilizing device 115 is arranged to stabilize the first instrument 210.

FIG. 5 shows a perspective view of the instrument advancing apparatus 100 according to the invention from a rear view. Here, further exemplary details of the instrument advancing apparatus 100 can be seen. For example, the instrument advancing apparatus 100 may include an accumulator 181 to provide power to at least the motors 120, 130 and 140. Further, the instrument advancing apparatus 100 may include a receiver 182 by means of which the motors 120, 130, and 140 are configured to be operable wirelessly. In FIG. 5, the accumulator 181 and the receiver 182 are exemplarily arranged on the fine positioning device 500 by omitting a cover arranged on the housing thereof. Therefore, cables 129, 139, and 149 are configured toward the first, second, and third motors 120, 130, and 140, respectively. For example, the accumulator 181 and/or the receiver 182 could also be arranged on the guide device 110. Then, accordingly, an embodiment with fewer or no cables would be conceivable.

Figures 6, 7:
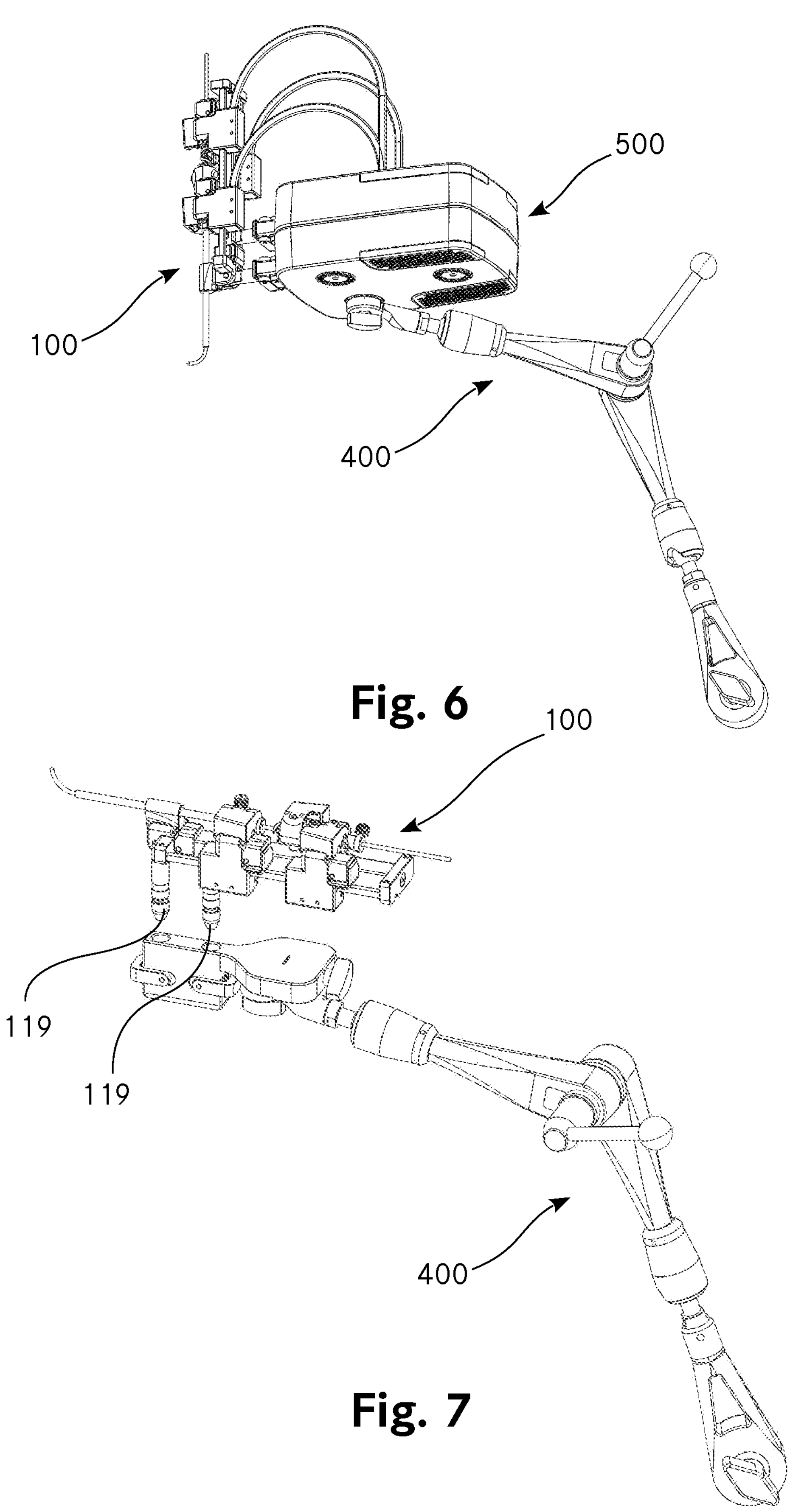
FIG. 6 depicts a perspective view of the instrument advancing apparatus according to the invention mounted on a fine positioning device, wherein the fine positioning device is mounted on a positioning arm.
FIG. 7 depicts a perspective view of the instrument advancing apparatus according to the invention, which is directly attachable to a positioning arm.

FIG. 6 and FIG. 7 show perspective views of the instrument advancing apparatus 100 according to the invention in various installation situations. In FIG. 6, the instrument advancing apparatus 100 is attached to the fine positioning device 500. The fine positioning device 500, in turn, is exemplarily attached to the positioning arm 400, the three joints of which can be centrally locked or released by means of a ratchet engaging the middle joint. In FIG. 7, on the other hand, the instrument advancing apparatus 100 is directly attachable to the positioning arm 400. For this purpose, the instrument advancing apparatus 100 has, by way of example, two fastening elements 119. The two fastening elements 119 are configured in the form of pins and can be inserted into corresponding recesses of an adapter on the positioning arm 400.

Figure 8:
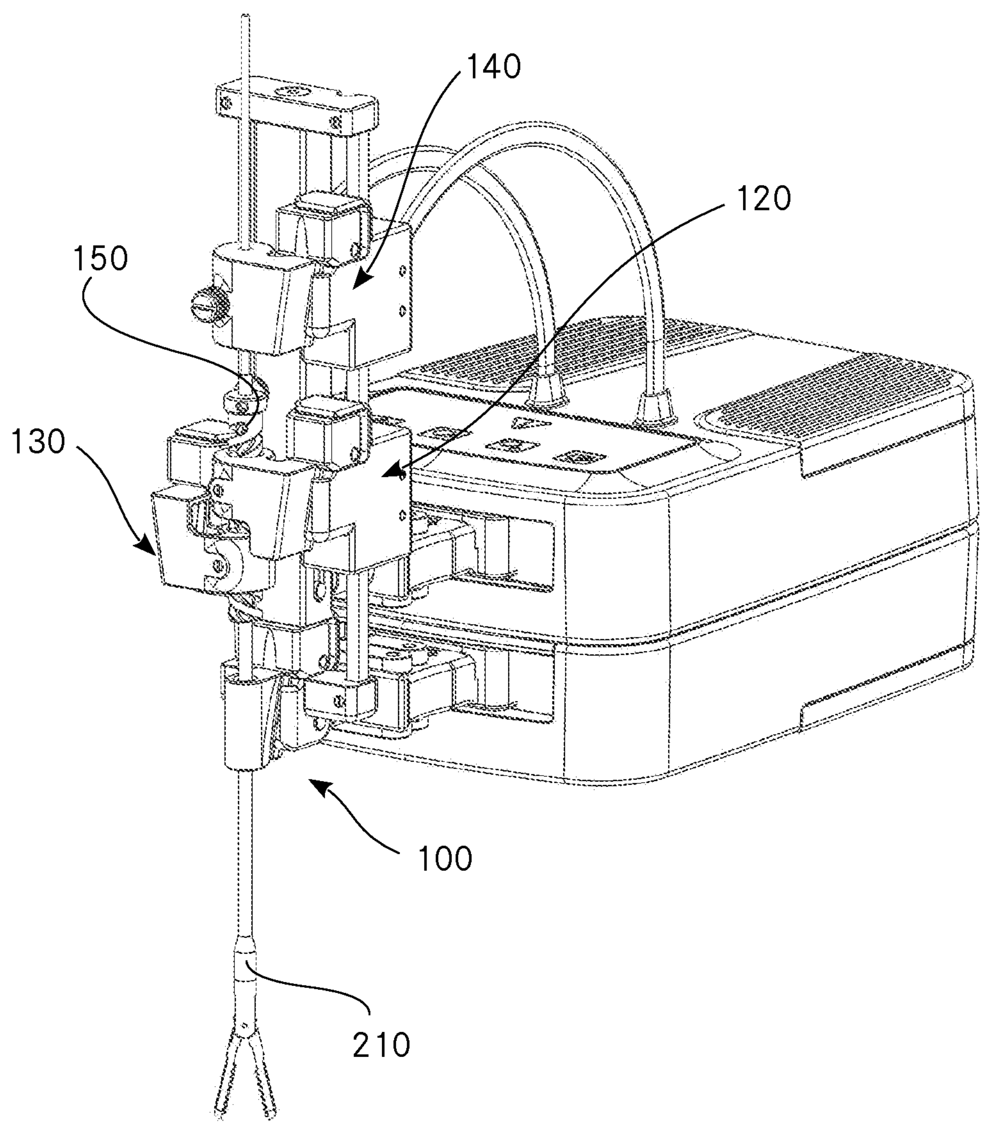
FIG. 8 depicts a perspective view of another instrument advancing apparatus according to the invention with forceps as the first instrument.
Figure 9:
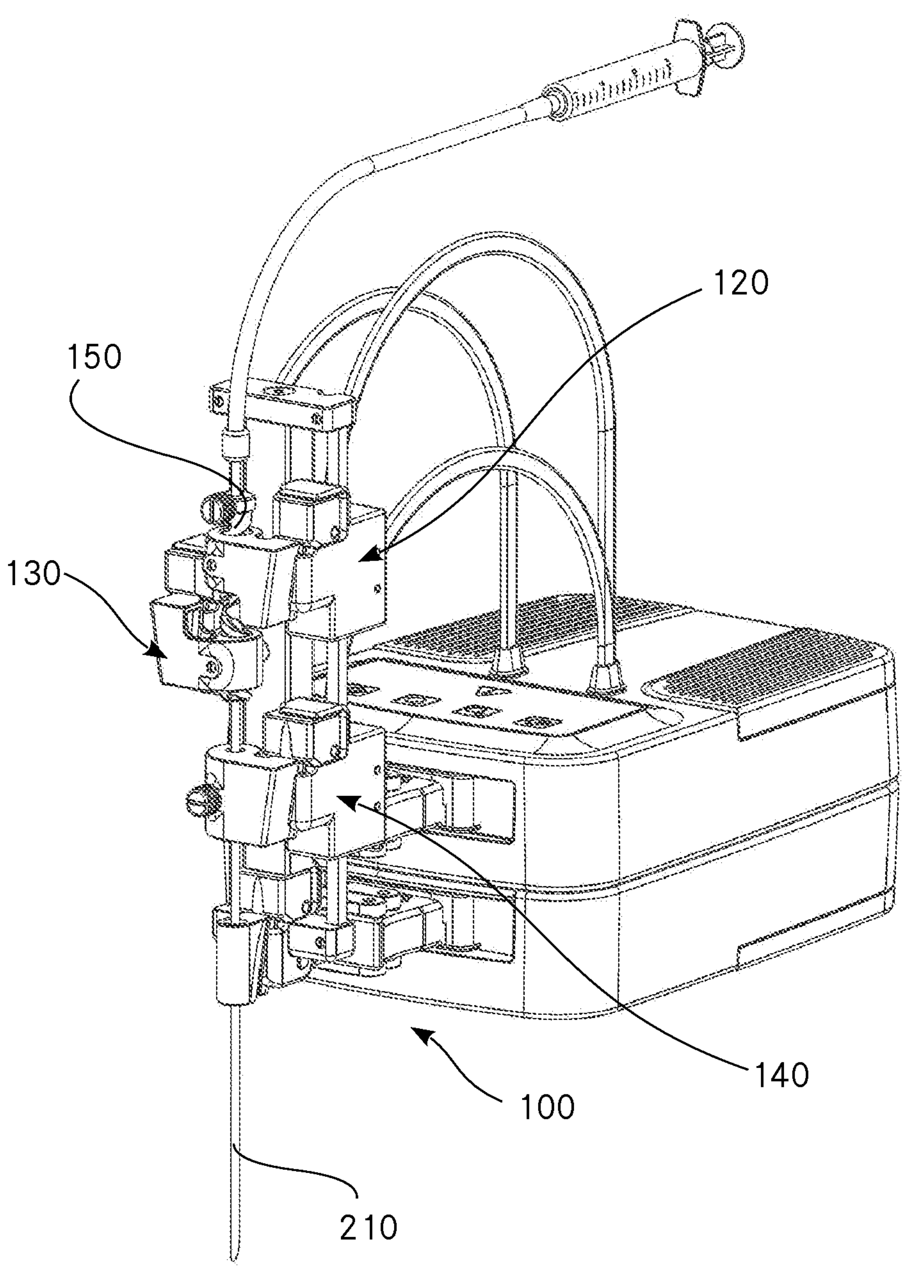
FIG. 9 depicts a perspective view of a further instrument advancing apparatus according to the invention with an injection needle as the first instrument.

FIGS. 8 and 9 show perspective views of different instrument advancing apparatuses 100 according to the invention, which differ in particular by their instruments. In FIG. 8, the first instrument 210 is forceps and in FIG. 9, the first instrument 210 is an injection needle. It is also apparent in FIGS. 8 and 9 that, depending on the application, the third motor 140 may be arranged above (FIG. 8) or below (FIG. 9) the other two motors 120 and 130.

FIGS. 10 to 15 show perspective views of instrument advancing apparatuses 100 according to the invention with their motors 120, 130 and 140 in different positions. By means of these figures, the movements of the motors 120, 130 and 140 can be shown particularly well.

Figures 10, 11:
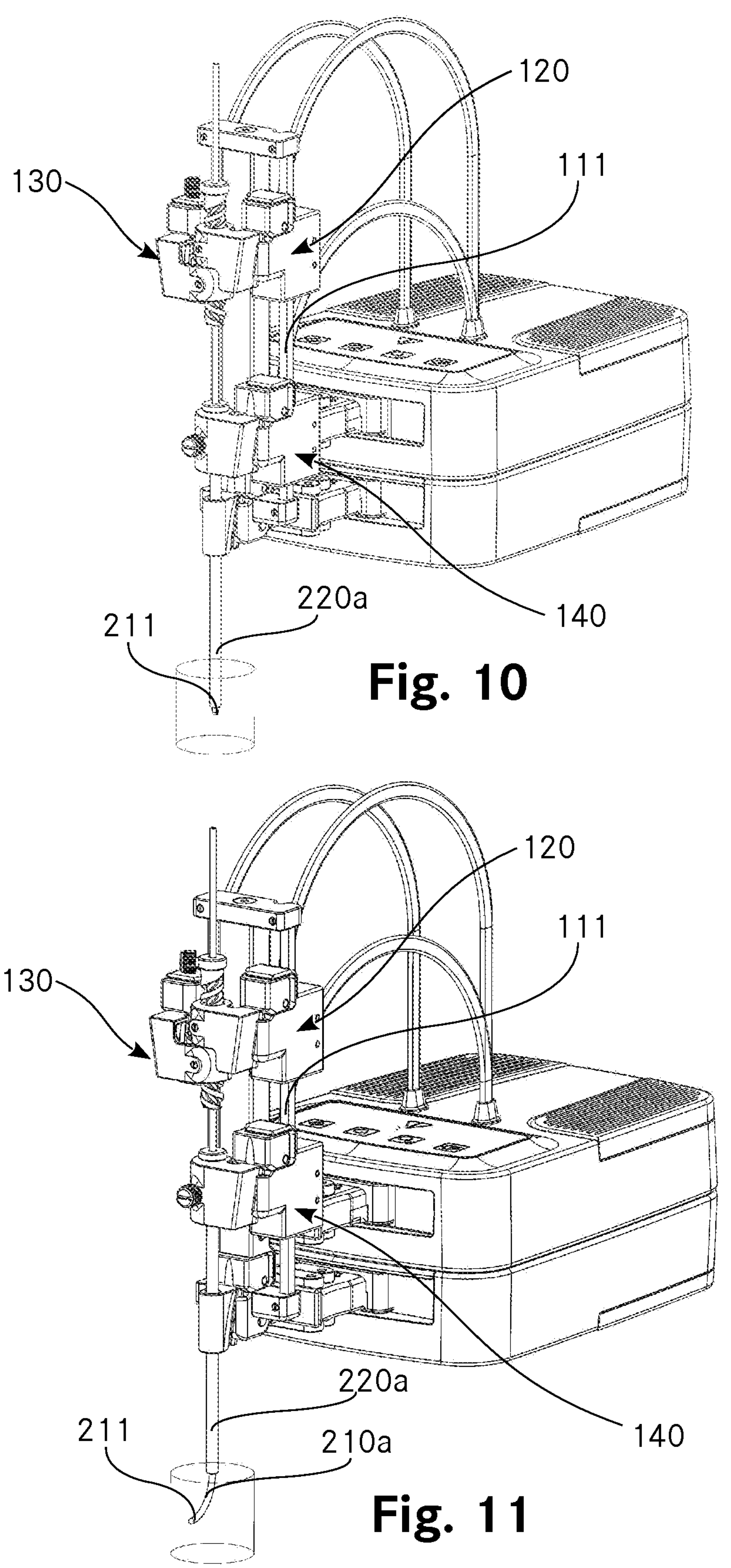
FIG. 10 depicts a perspective view of an instrument advancing apparatus according to the invention with a third motor in a lower position.
FIG. 11 depicts a perspective view of an instrument advancing apparatus according to the invention with a third motor in an upper position.

In FIG. 10, the third motor 140 that moves the tubular instrument **220*a* is in a lower position. When the third motor 140 is moved upward along the first axis body 111, the tubular instrument 220*a* moves upward together with the third motor 140. For example, the leading end 211 of the needle-shaped instrument 210*a* can be exposed. The upward position of the third motor 140 is shown in FIG. 11. The motors 120 and 130 are not moved from FIG. 10 to FIG. 11**.

Figures 12, 13:
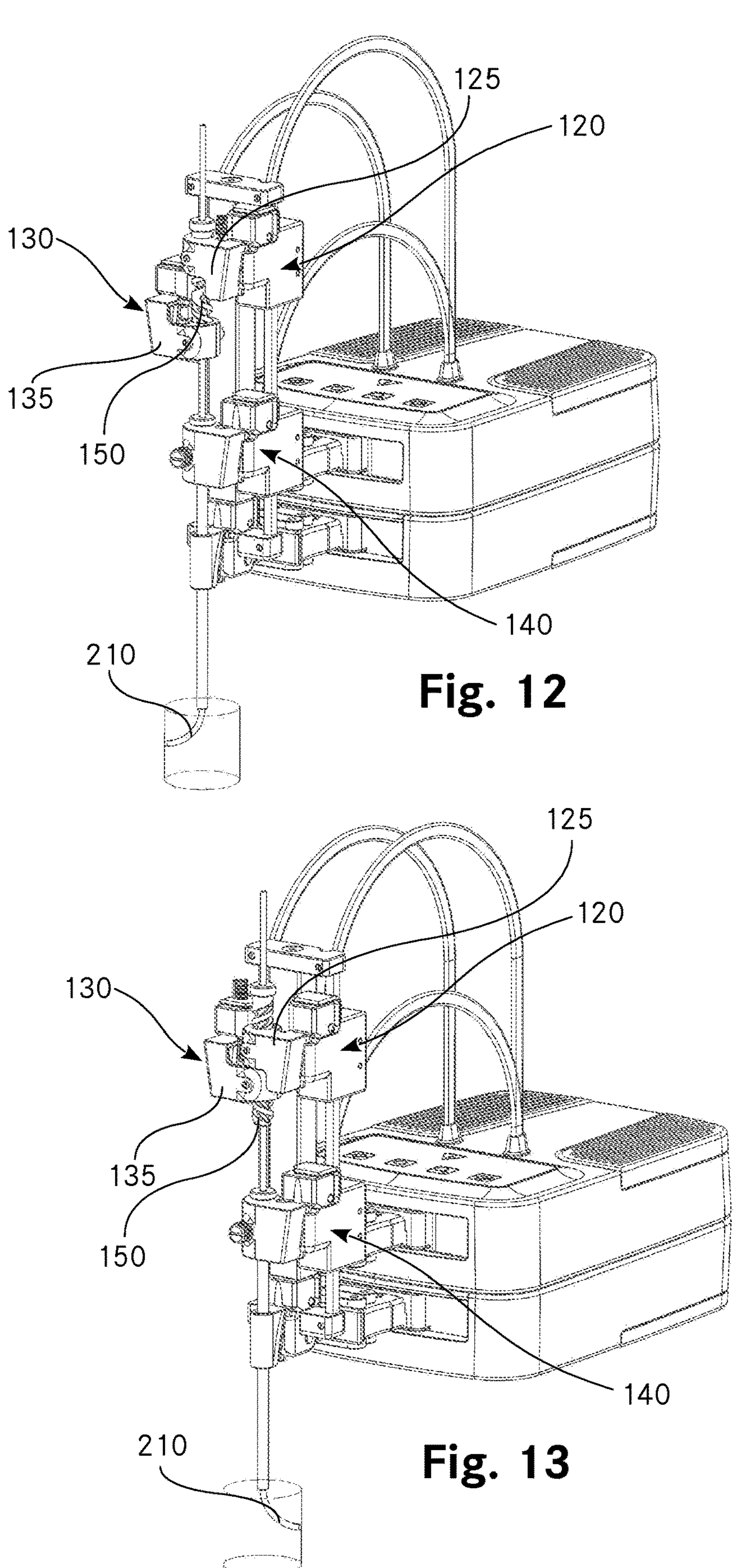
FIG. 12 depicts a perspective view of an instrument advancing apparatus according to the invention with a first and second motor in a spaced apart position.
FIG. 13 depicts a perspective view of an instrument advancing apparatus according to the invention, with a first and a second motor in a close together position.

In the perspective views of the instrument advancing apparatus 100 according to the invention shown in FIGS. 12 and 13, the rotating movement of the first instrument 210 is shown. For this purpose, the first motor 120 and the second motor 130 move towards each other from their spaced apart position in FIG. 12 to their close together position in FIG. 13. The first holding means 125 and the second holding means 135 are operatively connected to the spindle 150. If the two holding means 125 and 135 are moved in different directions, as subsequently shown in FIG. 12 and FIG. 13, this causes rotation of the spindle 150, which in turn causes rotation of the first instrument 210. Moving only one of the motors 120 and 130 would also cause such rotation of the first instrument 210. The third motor 140 does not move from FIG. 12 to FIG. 13.

Figures 14, 15:
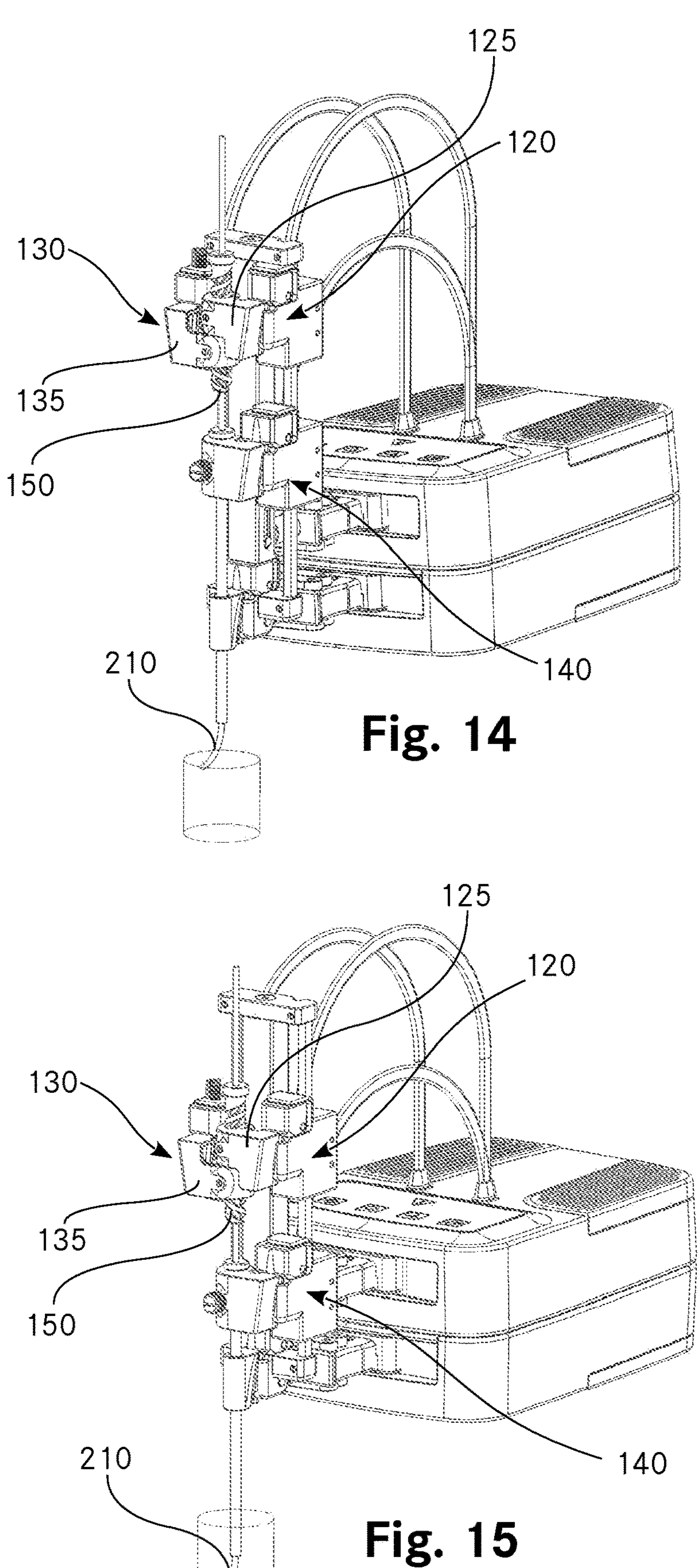
FIG. 14 depicts a perspective view of an instrument advancing apparatus according to the invention with a first, second and third motor in an upper position.
FIG. 15 depicts a perspective view of an instrument advancing apparatus according to the invention with a first, second and third motor in a lower position.

FIGS. 14 and 15 show simultaneous movement of all three motors 120, 130 and 140. Here, motors 120, 130, and 140 are in an upper position in FIG. 14. When the motors 120, 130 and 140 are moved downward, they are in the lower position shown in FIG. 15. In this case, the first instrument 210 and the second instrument 220 are moved down together.

Figure 16:
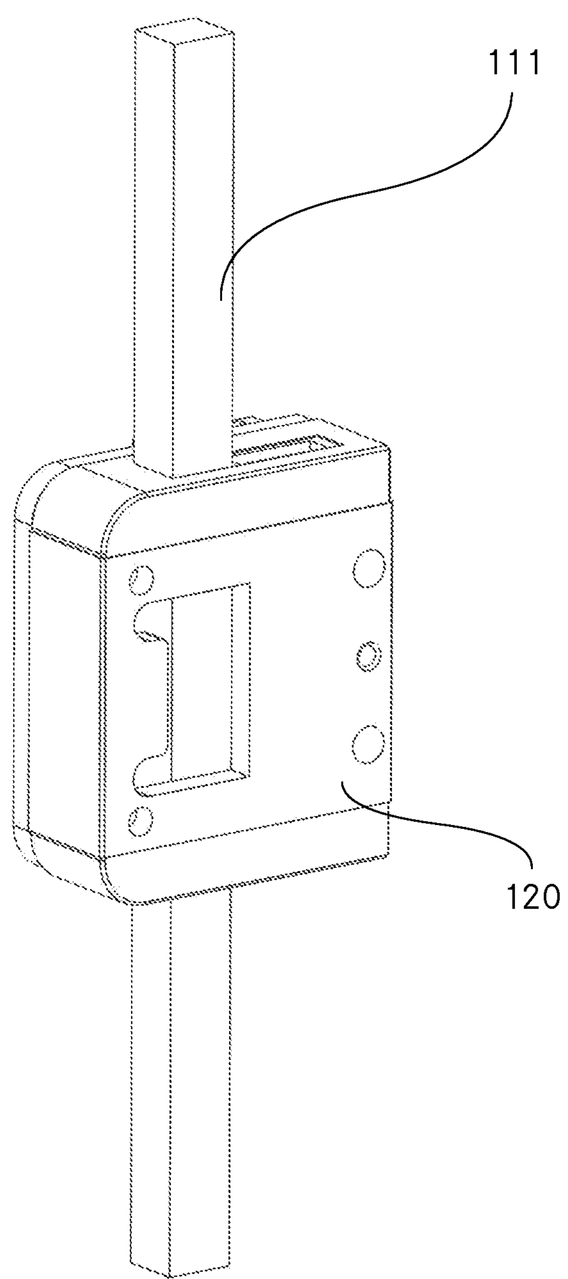
FIG. 16 depicts a detailed view of the first motor on the first axis body.

FIG. 16 shows a detailed view of the first motor 120 without a housing on the first axis body 111. In particular, the first motor 120 is configured to move along the axis body 111. For this purpose, the axis body 111 is inserted through the motor 120 or the first motor 120 is arranged around the axis body 111 so that the axis body 111 protrudes from an upper side of the first motor 120 and from a lower side of the first motor 120. As shown, the axis body 111 is preferably configured as a square axis. Sensors may be configured along the axis body 111 to determine the position of the motor 120 relative to the axis body 111, or vice versa. The first motor 120 is preferably a piezomotor, the operation of which is shown in detail on the website https://piezomotor.com/technology/ or in the youtube film that can be viewed there https://www.youtube.com/watch?v=7iHL4ZCkCKc&t=18s.

Figures 17, 18:
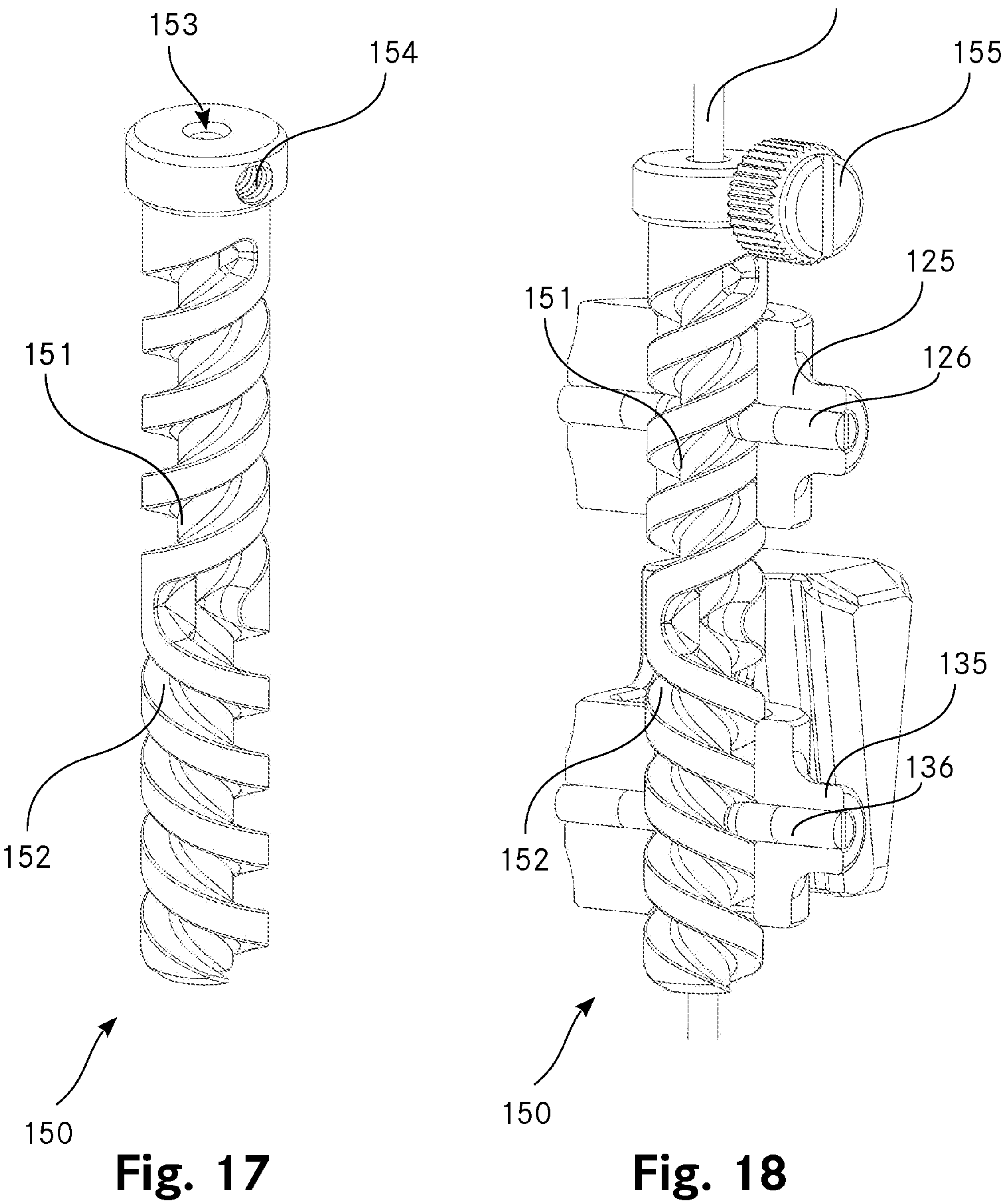
FIG. 17 depicts a detail view of a spindle device of an instrument advancing apparatus according to the invention.
FIG. 18 depicts a detailed view of a spindle device of an instrument advancing apparatus according to the invention with holding means shown in section.

FIGS. 17 and 18 show detailed views of the spindle device 150 with (FIG. 17) and without (FIG. 18) holding means 125, 135. The spindle device 150 is configured as a hollow body, in particular a hollow cylinder, with a cavity 153 in which the first instrument 210 can be arranged and fixed. For fixing the first instrument 210, a fixing device 155 can be used, as shown in FIG. 18. The fixing device 155 is configured, for example, as a fixing screw and is fastened in a threaded hole 154.

The spindle device 150 has two threads 151 and 152. In this case, one thread 151 is configured in an upper region, in particular an upper half, of the spindle device 150 and the other thread 152 is configured in a lower region, in particular a lower half, of the spindle device 150. The two threads 151 and 152 are configured to be counter-rotating.

As can be seen in FIG. 18, the first holding means 125 has a guide member 126 and the second holding means 135 has another guide member 136. Here, the guide member 126 is guided in the thread 151 and the other guide member 136 is guided in the other thread 152. As can be seen in FIG. 18, the guide members 126, 136 can be configured in the shape of a pin. Particularly preferably, as shown in FIG. 18, each of the holding means 125, 135 has two opposite, in particular pin-shaped, guide members 126, 136, between which the spindle device 150 is arranged.

By means of the two counter-rotating threads 151, 152, it is easily possible to transmit both a rotary motion and a translatory motion through the spindle device 150. If the two holding means 125 and 135 are moved in different directions, the spindle device 150 rotates. If the two holding means 125, 135 are moved at the same speed in the same direction, the spindle device 150 does not rotate but moves translationally.

Figures 19, 20:
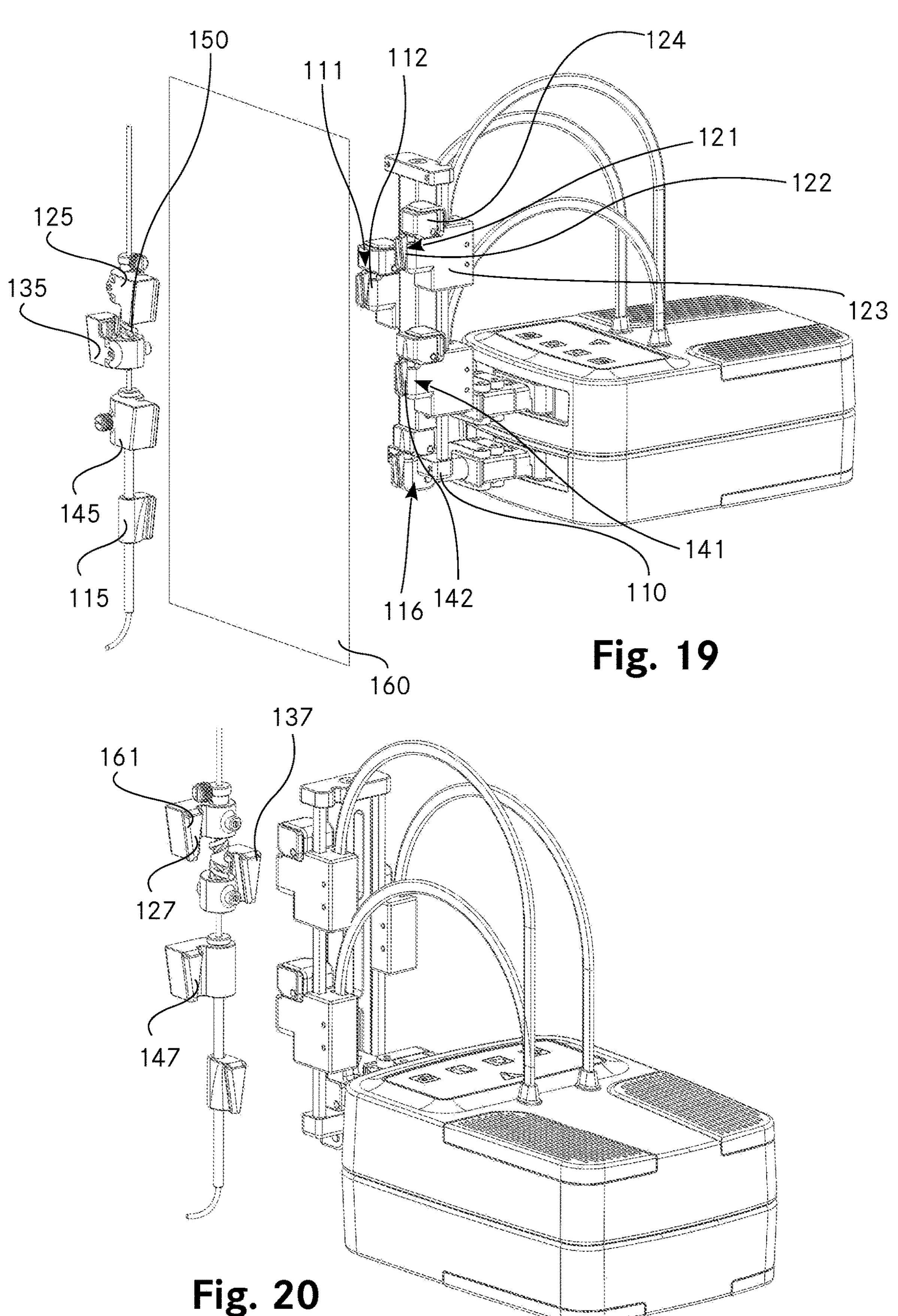
FIG. 19 depicts a perspective view of an instrument advancing apparatus according to the invention with holding means separate from the instrument advancing apparatus and a sterile film.
FIG. 20 depicts a perspective view of an instrument advancing apparatus according to the invention with holding means separate from the instrument advancing apparatus and without sterile foil.

FIG. 19 shows a perspective view of the instrument advancing apparatus 100 according to the invention with holding means 125, 135, 145 separate from the instrument advancing apparatus 100, with instrument stabilizing means 115 separate from the instrument advancing apparatus 100, with spindle 150 separate from the instrument advancing apparatus 100, and with instruments 210 and 220 separate from the instrument advancing apparatus 100. The elements separate from the instrument advancing apparatus 100, in particular the spindle device 150 and the holding means 125, 135 and 145, are preferably configured as disposables.

Between the separated elements, in particular the spindle device 150 and the holding means 125, 135 and 145, on one side and the remaining part of the instrument advancing apparatus 100, in particular the motors 120, 130 and 140, on the other side, a sterile foil 160 is arrangeable. Thus, the remaining part of the instrument advancing apparatus 100 can be easily separated in a sterile manner by means of the foil 160. When the parts arranged outside the foil 160 are configured as disposable, a simple sterile concept can be achieved. All more expensive components, such as motors 120, 130 and 140, axis bodies 111, 112 or, for example, a controller are arranged behind the sterile film 160.

To ensure non-destructive clamping of the sterile film 160, both the holding means 125, 135 and 145 and the motors 120, 125 and 135 are configured accordingly. This is illustrated in more detail with reference to FIG. 19 and FIG. 20, in particular using the first motor 120 as an example.

Each motor 120, 130, 140 has a first part of a fastening means 121, 131, 141, namely a fastening unit 122, 132, 142 for releasably fastening the respective holding means 125, 135, 145. As can be seen in FIG. 19, the fastening unit 122 may be configured as part of a housing 123 of the motor 120. This is true for each of the motors 120, 130 and 140.

The fastening units 122, 132 and 142 are configured to interact with complementary shaped counter units 127, 137 and 147 configured as a second part of the fastening means 121, 131, 141. These counter units 127, 137 and 147 are arranged on the holding means 125, 135 and 145 and are well seen in FIG. 20.

In this example, the fastening unit 122, 132 and 142 is a receptacle. The counter unit 127, 137 and 147 are shaped bodies complementary to the respective fastening unit 122, 132 and 142. Representative of all fastening units 122, 132 and 142, fastening unit 122 is adapted to receive counter unit 127. For this purpose, the counter unit 127 is configured to slide into the fastening unit 122 from one side, in this case from above. A push button 124 can act as a latching means to ensure secure retention of the counter unit 127 in the fastening unit 122. By actuating the push button 124, the counter unit 127 can be easily released from the fastening unit 122 again. Preferably, the fastening units 122, 132 and 142 are all configured in the same way. Thus, all counter units 127, 137 and 147 are also preferably configured the same. In this way, costs can be saved by using identical parts. As can be seen in FIGS. 19 and 20, the instrument stabilizing device 115 can also be fastened to the guide device 110 by means of a corresponding fastening means 116. The fastening means 116 is here preferably constructed in the same way as the fastening means 121, 131, 141 described above.

As can be seen on closer look at the fastening means 121, 131, 141 and 116, the respective fastening units 122, 132, 142 and counter units 127, 137 and 147 have rounded corners and edges 161. This is exemplified in FIG. 20 in the case of counter unit 127. This allows the sterile film 160 to be clamped non-destructively between the fastening units 122, 132, 142 and the counter units 127, 137 and 147.

Figure 21:
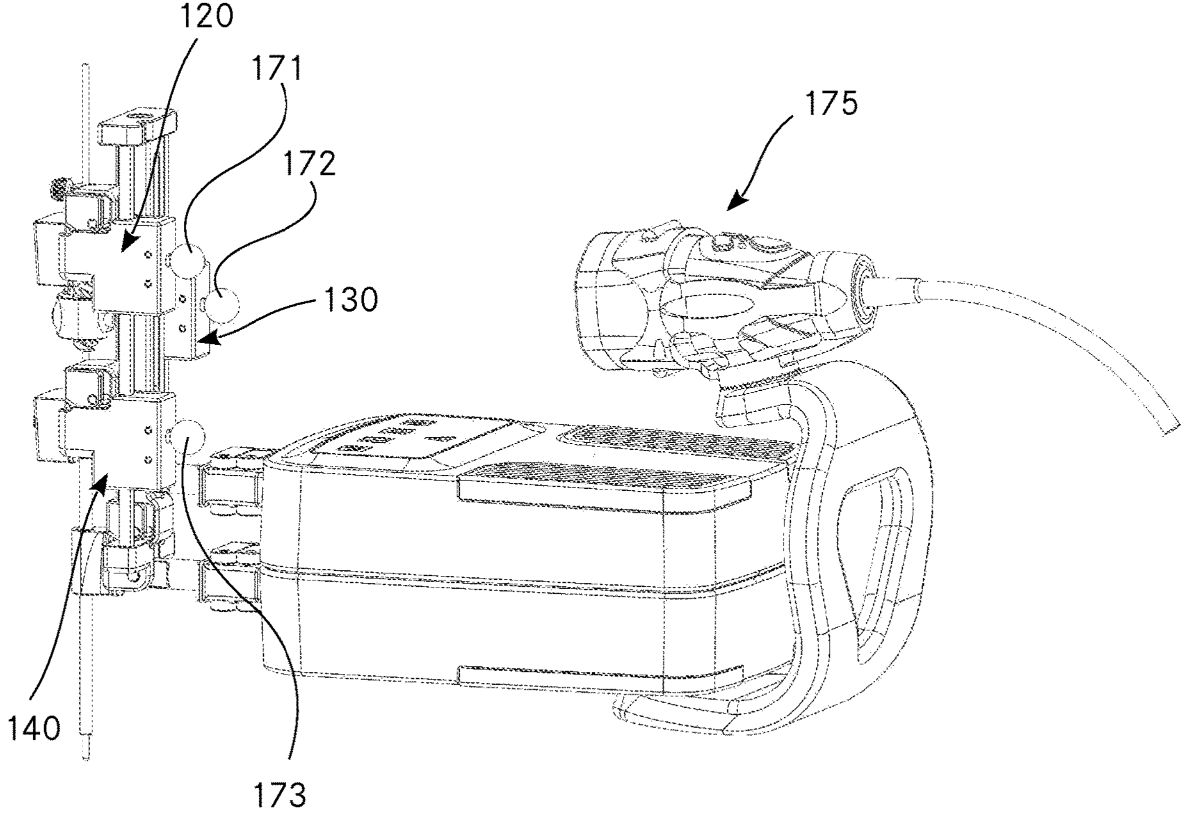
FIG. 21 depicts a perspective view of an instrument advancing apparatus according to the invention with a sensor system.

FIG. 21 shows a perspective view of the instrument advancing apparatus 100 according to the invention with a sensor system. Preferably, a sensor 171, 172 and 173 is assigned to each motor 120, 130 and 140. In particular, a first sensor 171 is arranged at the first motor 120, a second sensor 172 is arranged at the second motor 130, and a third sensor 173 is arranged at the third motor 140. The sensors 171, 172, 173 shown are exemplary optical markers that can be detected by means of a camera 175. In particular, the sensor system is an inside-out system in which the camera 175 observes from within the system. Alternatively, an outside-in approach would also be conceivable, in which the camera 175 is arranged outside the system and observes the system from outside.

In particular, the camera 175 can be used to detect the relative positions and thus the movements of the motors 120, 130 and 140 with respect to each other. The embodiment using camera 175 and optical markers is purely exemplary. Alternatively, the sensors 171, 172, 173 could be Hall sensors and magnets or RFID chips, for example.

Particularly preferably, the sensor system is configured redundantly, i.e. comprises a second sensor arrangement in addition to the first sensor arrangement shown. The second sensor arrangement is furthermore preferably based on a principle different from the first sensor arrangement. For example, the second sensor arrangement may be Hall sensors and magnets or RFID chips.

It should be noted that the features of the invention described with reference to individual embodiments or variants, such as the type and design of the individual components and their precise dimensioning and spatial arrangement, may also be present in other embodiments, except where otherwise indicated or where it is self-evident for technical reasons. Moreover, of such features of individual embodiments described in combination, not necessarily all features must always be realized in a respective embodiment.

The invention claimed is:

1. An instrument advancing apparatus for translationally and/or rotationally driving at least one first instrument, the instrument advancing apparatus comprising:

a guide device comprising at least one first axis body extending in a translational driving direction of the at least one first instrument, at least one first motor configured to be motor-driven along the first axis body; and at least one second motor configured to be motor-driven along the first axis body or along a second axis body of the guide device, the second axis body being aligned parallel to the first axis body, and wherein the first motor is connected or configured to be connectable to a first holding means configured to hold and/or move the first instrument, wherein the second motor is connected or configured to be connectable to a second holding means configured to hold and/or move the first instrument or a second instrument, wherein the instrument advancing apparatus comprises a spindle device configured to rotationally move the first instrument, and the spindle device operatively connected to at least one of the first holding means, the second holding means, and a third holding means, and wherein the spindle device comprises two counter-rotating threads.

2. The instrument advancing apparatus according to claim 1, wherein the instrument advancing apparatus further comprises at least a third motor configured to be motor-driven along the first axis body, along the second axis body, or along a third axis body of the guide device, the third axis body being aligned parallel to the first axis body and the second axis body.

3. The instrument advancing apparatus according to claim 2, wherein the third motor comprises the third holding means configured to hold and/or move first instrument or the second instrument.

4. The instrument advancing apparatus according to claim 2, wherein the first motor, the second motor and the third motor are piezo motors.

5. The instrument advancing apparatus according to claim 2, wherein the first motor, the second motor and the third motor each comprise a fastening means configured to releasably fasten the first holding means, the second holding means and the third holding means.

6. The instrument advancing apparatus according to claim 5, wherein the fastening means comprise a fastening unit configured to interact with a complementarily shaped counter unit of the first holding means, the second holding means and the third holding means.

7. The instrument advancing apparatus according to claim 1, wherein the spindle device is configured to interact with the first holding means and the second holding means.

8. The instrument advancing apparatus according to claim 1, wherein the spindle device comprises a hollow body including a cavity and at least one thread, wherein the first instrument is configured to be arranged and fixed in the cavity.

9. The instrument advancing apparatus according to claim 8, wherein the first holding means and/or the second holding means comprises a guide member configured to be guided in the at least one thread.

10. The instrument advancing apparatus according to claim 1, wherein the first instrument and/or the second instrument are medical instruments.

11. The instrument advancing apparatus according to claim 1, wherein the first instrument is a needle-shaped instrument and the second instrument is a tube-shaped instrument, and wherein the first instrument is configured and arranged to pass through the second instrument.

12. The instrument advancing apparatus according to claim 1, wherein the guide device comprises an instrument stabilizing device configured to stabilize a leading end of the first instrument or the second instrument.

* * * * *